(12) United States Patent
Keenan et al.

(10) Patent No.: US 11,937,827 B2
(45) Date of Patent: Mar. 26, 2024

(54) DEVICE AND METHOD FOR TREATMENT OF HEMORRHOIDS

(71) Applicant: BOSTON SCIENTIFIC SCIMED, INC., Maple Grove, MN (US)

(72) Inventors: Daniel Keenan, Charlton, MA (US); Briana Jean Moretti, Franklin, MA (US); Jacqueline Nicole Magaha, Taneytown, MD (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 787 days.

(21) Appl. No.: 16/947,202

(22) Filed: Jul. 22, 2020

(65) Prior Publication Data

US 2021/0022596 A1 Jan. 28, 2021

Related U.S. Application Data

(60) Provisional application No. 62/877,960, filed on Jul. 24, 2019.

(51) Int. Cl.
*A61B 17/122* (2006.01)
*A61B 1/00* (2006.01)
*A61B 1/06* (2006.01)
*A61B 1/31* (2006.01)
*A61B 17/12* (2006.01)

(52) U.S. Cl.
CPC ........ *A61B 17/122* (2013.01); *A61B 1/00066* (2013.01); *A61B 1/00094* (2013.01); *A61B 1/00148* (2022.02); *A61B 1/0684* (2013.01); *A61B 1/31* (2013.01); *A61B 17/12013* (2013.01); *A61B 2017/12018* (2013.01)

(58) Field of Classification Search
CPC .............. A61B 17/122; A61B 1/00148; A61B 1/00066; A61B 1/00094; A61B 1/0684; A61B 1/31; A61B 17/12013; A61B 2017/12018
See application file for complete search history.

(56) References Cited

U.S. PATENT DOCUMENTS 3,760,810 A * 9/1973 Van Hoorn ...... A61B 17/12013
606/140
7,210,609 B2 5/2007 Leiboff et al.
(Continued)

FOREIGN PATENT DOCUMENTS

CA 3001224 A1 * 11/2018 ........... A61B 17/083
CN 101547654 9/2009
(Continued)

*Primary Examiner* — Katherine H Schwiker
*Assistant Examiner* — Zehra Jaffri
(74) *Attorney, Agent, or Firm* — Fay Kaplun & Marcin, LLP

(57) ABSTRACT

A device includes including an elongated hollow member with a window for receiving tissue in an interior of the hollow member; a rigid member slidably coupled to the hollow member; and an actuation mechanism configured to move the rigid member longitudinally along a longitudinal axis through at least part of the window. When a ligation band is adjacent to the window and the rigid member is moved relative to the hollow member, the rigid member deforms the ligation band from an open position into a closed position around tissue received in the window.

18 Claims, 8 Drawing Sheets

(56) References Cited

U.S. PATENT DOCUMENTS

| | | | |
|---|---|---|---|
| 7,892,244 B2* | 2/2011 | Monassevitch | A61B 17/1285 606/151 |
| 9,232,947 B2* | 1/2016 | Brenner | A61B 5/415 |
| 9,619,145 B2* | 4/2017 | Durham | G06F 3/0604 |
| 2006/0009797 A1* | 1/2006 | Armstrong | A61B 1/00071 606/197 |
| 2006/0167473 A1 | 7/2006 | Scheyer | |
| 2006/0271103 A1 | 11/2006 | Ferrari | |
| 2008/0249546 A1* | 10/2008 | Sandstrom | A61B 17/115 606/153 |
| 2008/0262511 A1 | 10/2008 | Delaney | |
| 2010/0023023 A1* | 1/2010 | Popovic | A61B 17/068 606/151 |
| 2010/0213239 A1* | 8/2010 | Rebuffat | A61B 17/1155 227/180.1 |
| 2017/0071620 A1 | 3/2017 | Piskun | |

FOREIGN PATENT DOCUMENTS

| | | | |
|---|---|---|---|
| EP | 536882 A2 * | 4/1993 | A61B 17/115 |
| EP | 1983906 | 10/2008 | |
| EP | 2398548 | 3/2013 | |
| EP | 2692282 | 2/2014 | |
| EP | 2770931 | 3/2017 | |
| WO | 2007/093198 | 8/2007 | |
| WO | 2010/096174 | 8/2010 | |
| WO | 2013/062652 | 5/2013 | |
| WO | WO-2017106933 A1 * | 6/2017 | A61B 17/12009 |

* cited by examiner

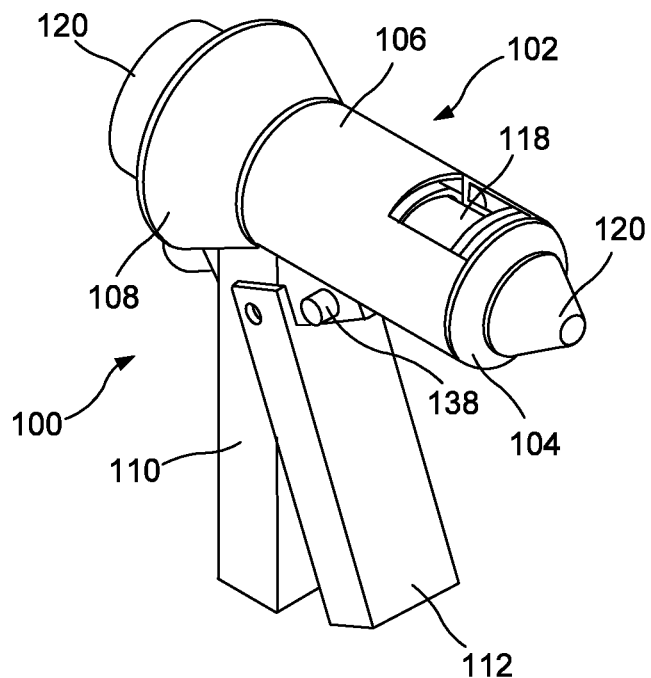
F I G. 1
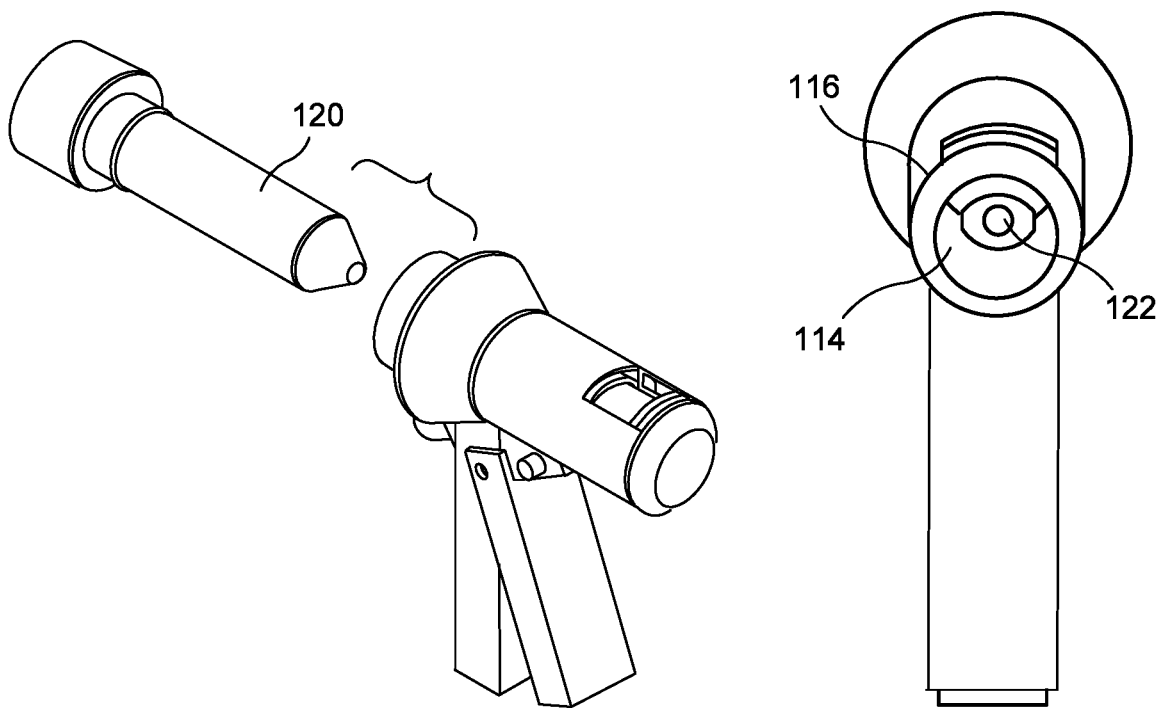
F I G. 2
F I G. 3

DEVICE AND METHOD FOR TREATMENT OF HEMORRHOIDS

PRIORITY CLAIM

The present disclosure claims priority to U.S. Provisional Patent Application Ser. No. 62/877,960 filed Jul. 24, 2019; the disclosure of which is incorporated herewith by reference.

FIELD

The present invention relates to a device and a method for treatment of hemorrhoids and, in particular, band ligation fully compatible with an anoscope.

BACKGROUND

Hemorrhoids are swollen and inflamed veins around the anus or in the lower rectum.

Hemorrhoids may be external, forming under the skin around the anus, or internal, forming in the lining of the anus and the lower rectum. Ligation is a common method for treating hemorrhoids. In ligation, a band or other device is placed around the base of the hemorrhoid strangulating blood flow thereto, reducing inflammation and eventually eliminating the hemorrhoid. Bands may be e.g. rubber or metal.

Commercially available anoscopes allow physicians to visualize and access the anal cavity while treating a patient.

SUMMARY

The present disclosure relates to a device includes an elongated hollow member with a window for receiving tissue in an interior of the hollow member; a rigid member slidably coupled to the hollow member; and an actuation mechanism configured to move the rigid member longitudinally along a longitudinal axis through at least part of the window. When a ligation band is adjacent to the window and the rigid member is moved relative to the hollow member, the rigid member deforms the ligation band from an open position into a closed position around tissue received in the window.

In an embodiment, the device further includes a dilator configured to be inserted into the hollow member.

In an embodiment, the device further includes a light source directed towards the window.

In an embodiment, the ligation band is made of a metal.

In an embodiment, the ligation band is curved into a C-shape with an open side.

In an embodiment, the ligation band is loaded with the open side of the C-shape facing distally towards the window, the C-shape being formed of a lateral side with two longitudinal sides extending from either end of the lateral side.

In an embodiment, the ligation band is loaded with the open side of the C-shape directed laterally sideways with respect to the longitudinal axis, the C-shape being formed of a longitudinal side with two lateral sides extending from either end of the longitudinal side.

In an embodiment, the hollow member includes a tapered distal portion, a flared proximal base portion, and an elongated middle portion.

In an embodiment, the hollow member includes an inner cylinder and an outer cylinder separated from one another via an annular space.

In an embodiment, the device further includes a crimp plate channel extending from a proximal end of the window to a distal end of the window.

In an embodiment, the device further includes a ligation band channel extending from a proximal end of the middle portion to a proximal end of the window, opening into the window.

In an embodiment, the rigid member includes a ring-shaped crimp plate housed in the crimp plate channel.

In an embodiment, the device further includes indents located in the crimp plate configured to deform the ligation band into a predetermined pattern.

In an embodiment, the ligation band channel is configured to house a plurality of ligation bands.

In an embodiment, the device further includes a safety stop located on the actuation mechanism to prevent deformation of the ligation band during loading and prior to deployment.

The present disclosure also relates to a method which includes inserting into an anal cavity, a device includes an elongated hollow member, the hollow member including a window for receiving tissue in an interior of the hollow member; and actuating an actuation mechanism of the device configured to move a rigid member longitudinally through at least part of the window, the rigid member being slidably coupled to the hollow member. When a ligation band is adjacent to the window and the rigid member is moved relative to the hollow member, the rigid member deforms the ligation band from an open position into a closed position around tissue received in the window.

In an embodiment, the method further includes inserting a dilator into the device through the hollow member prior to insertion of the device into the anal cavity; and removing the dilator after the device is inserted into a desired position.

In an embodiment, the method further includes illuminating a first target area via a light source to align the window of the hollow member with a first target portion of tissue.

In an embodiment, the method further includes releasing a safety stop on the actuation mechanism to move the rigid member longitudinally through at least part of the window.

In an embodiment, the method further includes visualizing a second target area; rotating the hollow member independently of the actuation mechanism; aligning the window with the second target area; drawing a second target portion of tissue into the device through the window; and actuating the actuation mechanism to deform the ligation band from the open position into the closed position around the second target portion of tissue

BRIEF DESCRIPTION

FIG. 1 shows a perspective view of an anoscope device for ligating hemorrhoids according to a first exemplary embodiment of the present disclosure.

FIG. 2 shows a perspective view of the device of FIG. 1 with a dilator removed.

FIG. 3 shows a front view of the device of FIG. 1.

DETAILED DESCRIPTION

Figure 4:
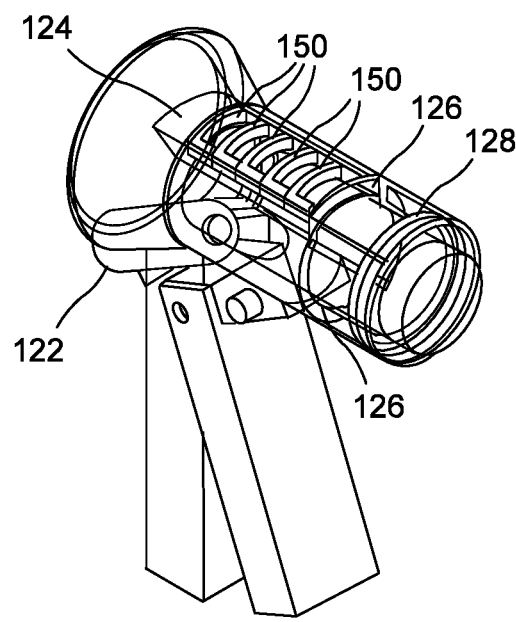
FIG. 4 shows a transparent perspective view of the device of FIG. 1.

The present disclosure may be further understood with reference to the following description and the appended drawings, wherein like elements are referred to with the same reference numerals. The present disclosure is directed to an anoscope device with a metal band ligation mechanism for ligating one or more hemorrhoids. The exemplary device may access the anal cavity, visualize a hemorrhoidal treatment area, and crimp a metal ligation band around the base of the one or more hemorrhoids. It is noted that the terms "proximal" and "distal," as used herein, refer to a direction toward (proximal) and away from (distal) a user of the device.

FIG. 1 shows an anoscope device 100 for performing a metal band ligation procedure. The anoscope device 100 includes an elongated body 102 with a tapered distal portion 104, a flared proximal base portion 108, and an elongated middle portion 106 therebetween. A handle 110 in this embodiment extends orthogonally from the body 102 with a trigger 112 for actuating a crimping mechanism during the ligation procedure as explained in more detail below. The body 102 has a hollow interior defined by an inner cylinder 114 extending through the middle 106 portion and the distal 104 portion of the body 102. The middle portion 106 has an outer cylinder 116 surrounding the exterior of and concentric with the inner cylinder 114 and defines an annular space therebetween in which components of the crimping mechanism are housed. A window 118 extends through the middle portion 106 adjacent to the distal portion 104 and opens into the interior of the device 100. During the ligation procedure a hemorrhoid may be received in the window 118 and a ligation band 150 may then be applied thereover.

The device 100 includes a removable dilator 120 sized to extend through the interior of the body 102 and out the distal end of the distal portion 104. The dilator 120 has a rounded conical distal end, an elongated shaft, and an enlarged proximal end. The elongated shaft of the dilator 120 has an outer diameter substantially corresponding to an inner diameter of the inner cylinder 114, such that the shaft slides therein. The enlarged proximal end of the dilator 120 cannot extend past the flared base portion 108 of the body 102 due to its size. The enlarged proximal end of the dilator 120 is positioned so that, when the enlarged proximal end of the dilator 120 abuts the flared base portion 108, only the conical distal end of the dilator 120 extends out of the distal end of the distal portion 104.

During the metal band ligation procedure the dilator 120 is used to expand the anus of a patient facilitating access for the device 100 to the anal cavity. Additionally, during insertion into the anal cavity, the dilator 120 prevents access to the interior of the body 102 of the device 100 via the window 118, i.e., the dilator 120 blocks the window 118. In this way, the operating physician will not capture non-targeted tissue in the window 118 prior to properly arranging the anoscope 100 with respect to the anatomy and target site. The interior of the body 102 may be opened to the anal cavity via the window 118 and the open end of the tapered distal portion 104 after the dilator 120 has been removed. The body 102 may be rotated independently of handle 110 so that the window 118 can be properly aligned with the target portion of tissue at the target site. A light source 122 arranged in the proximal end of the device 100 is directed toward the window 118. During the ligation procedure the light source 122 illuminates the anal cavity and the treatment area surrounding the hemorrhoid(s) to help the physician visualize the treatment area through the flared proximal base portion 108 facilitating placement of the device 100 and the window 118 in a desired location and orientation relative to the hemorrhoidal tissue.

Figure 5:
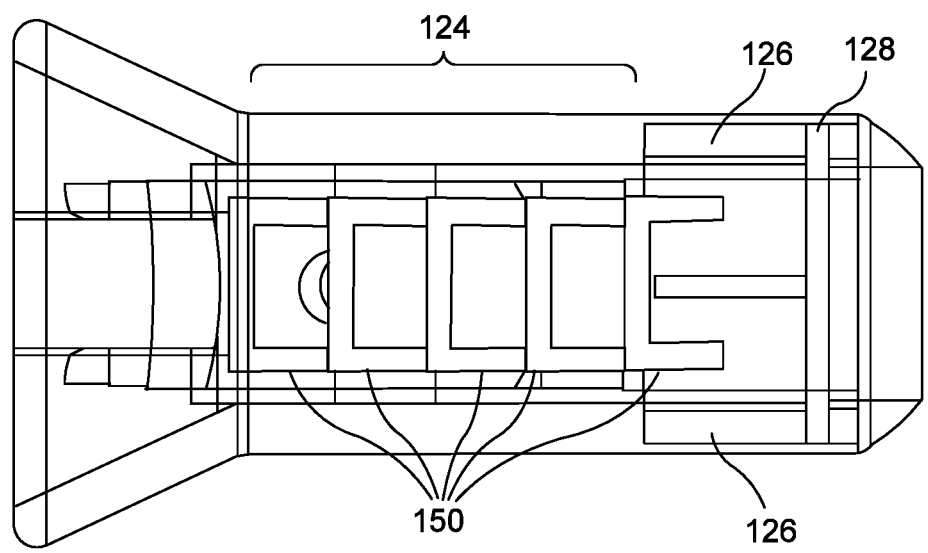
FIG. 5 shows a transparent top view of the device of FIG. 1.
Figure 6:
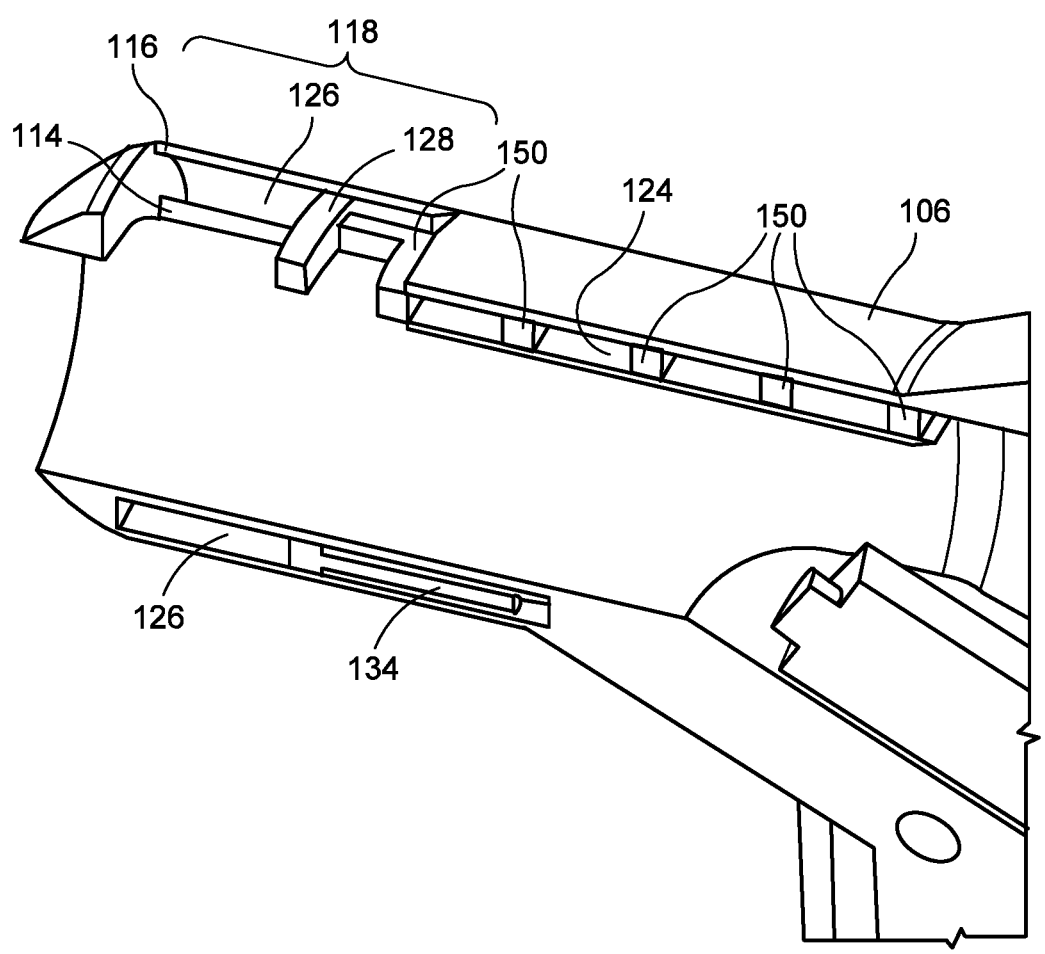
FIG. 6 shows a cross-sectional view including a band channel portion and a crimp ring channel portion of the device of FIG. 1.

Two channels are defined in portions of the space between the outer cylinder 116 and the inner cylinder 114. The remainder of the space may be open or may include structure for affixing the inner and outer cylinders 114, 116. A ligation band channel 124 at the top of the middle portion 106, as shown in FIG. 6, extends from the proximal end of the middle portion 106 to the proximal end of the window 118 and opens into the window area. The band channel 124 is sized to house a plurality of ligation bands 150. The present embodiment of the body 102 shown in, e.g., FIGS. 4-5, is loaded with five ligation bands 150, however, any number of bands may be used as would be understood by those skilled in the art. The bands 150 are preferably metal (e.g., 304SS), however, any material with comparable strength and deformation properties may be used.

In one embodiment, the ligation bands 150 are C-shaped with two longitudinal sides extending off of a lateral side. The lateral side of the C-shape is arced to rest on an exterior of the inner cylinder 114 when the band 150 is loaded in the channel 124. The two longitudinal sides of the C-shape are substantially straight. The bands 150 are loaded in the channel 124 with the open side of the C-shape facing distally toward the window 118. A plurality of bands 150 may be loaded into the channel 124 using a removable insert, or another sort of pushing element. The channel 124 provides clearance for the bands 150 to be inserted such that the bands 150 may slide. Alignment of the bands 150 and crimp mechanism are described in detail below.

Figure 7:
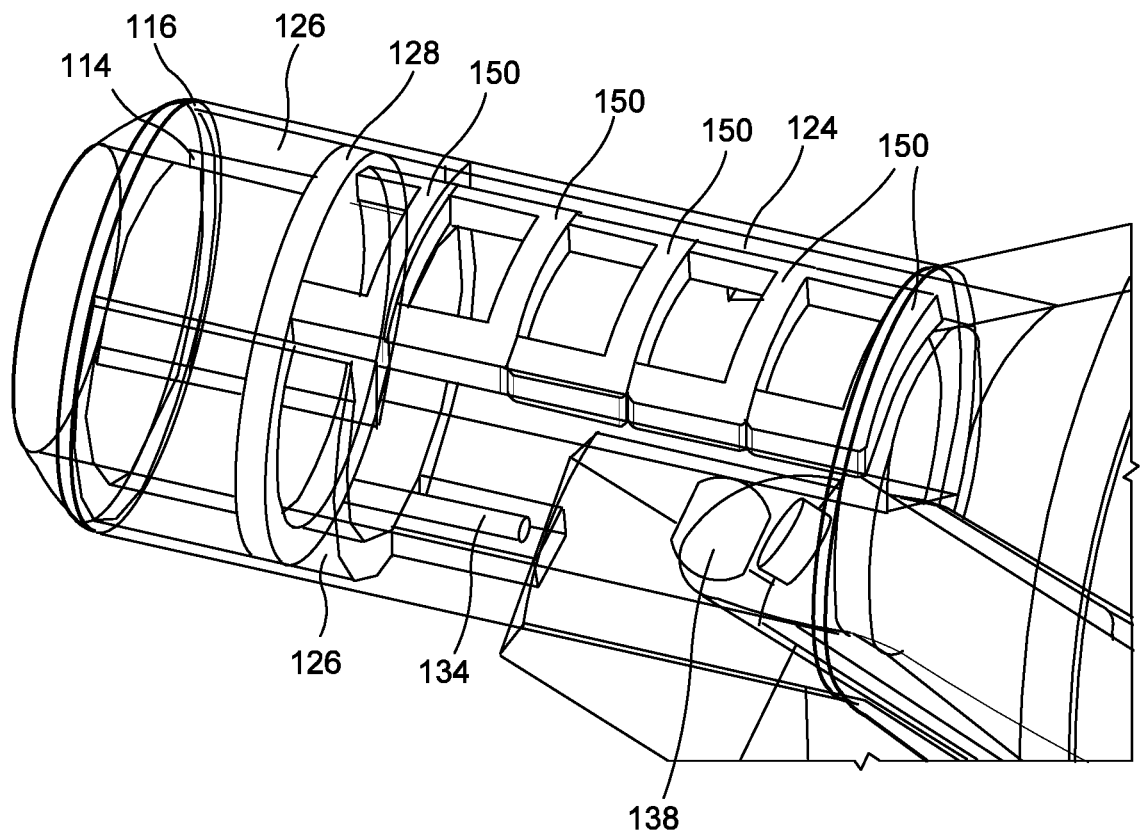
FIG. 7 shows a transparent perspective view including a band channel portion and a crimp ring channel portion of the device of FIG. 1.

A crimp plate channel 126 is defined as the annular space between the inner and outer cylinders 114, 116 extending from the proximal end of the window 118 to the distal end of the window 118. In other words, the crimp plate channel 126 is the portion of the space radially adjacent to the window 118. A cross-section of the channel 126 is shown in FIG. 6. A transparent view of the ligation band 124 and the crimp plate channel 126 is shown in FIG. 7. The channel 126 houses a ring-shaped crimp plate 128. When the device 100 is in an unactuated state the crimp plate 128 rests at the distal end of the channel 126 adjacent to the tapered distal end 104 of the body 102. Actuation of the crimping mechanism via the trigger 112 brings the plate 128 proximally through the channel 126, while release of the trigger 112 returns the plate 128 to its distal position. The crimp plate 128 may have indents 130, as shown in FIG. 8, to orient the deformation of a ligation band 150, to be described below.

Figure 9:
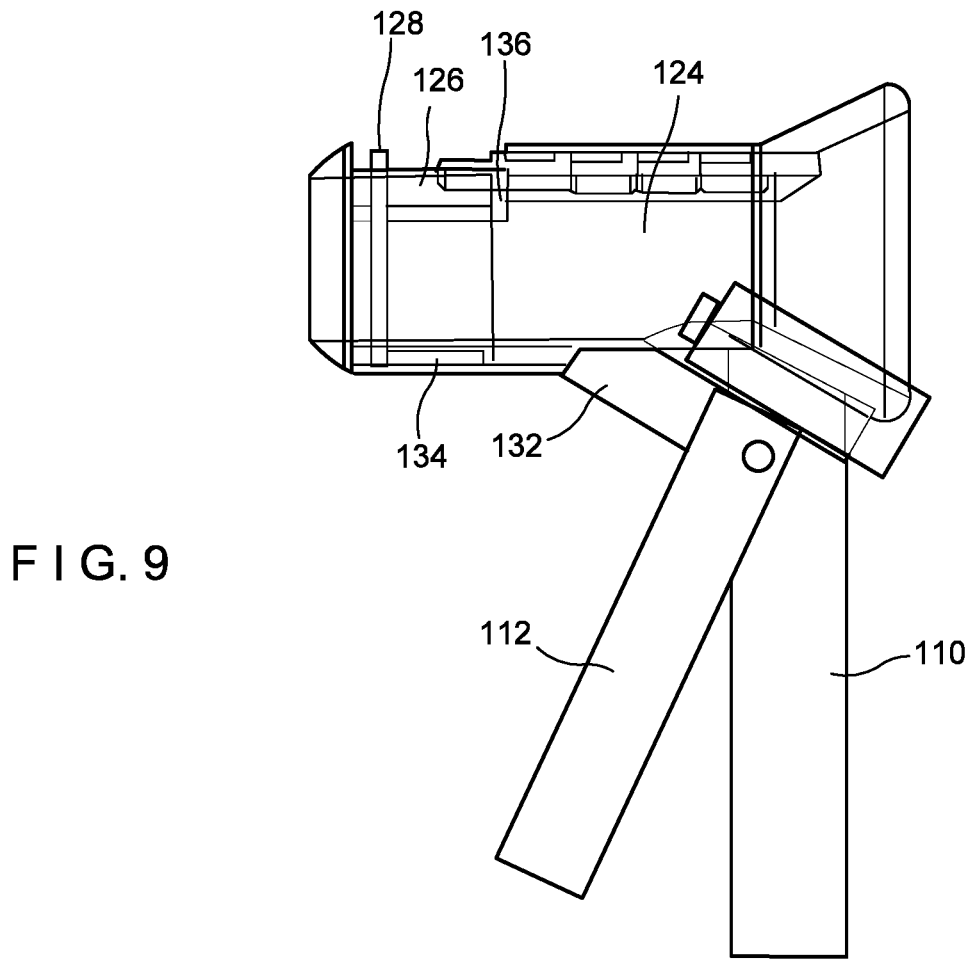
FIG. 9 shows a transparent side view of the device of FIG. 1 when the device is unactuated.

The crimping mechanism includes the crimp plate 128 and a linkage 132 in the trigger 112 for actuating the crimp plate 128 in the channel 126 via a pull member 134. The linkage 132 contains a safety stop button 138 which ensures that during loading and other procedural steps, the ligation bands 150 cannot be deployed prematurely. The pull member 134 extends from the linkage 132 in the handle 110 to the bottommost part of the crimp plate 128. The pull member 134 and the crimp plate 128 are connected so that they can only move back and forth. When the safety button 138 is released, the trigger 112 may be moved inward toward the handle 110 by a user. When the trigger 112 is actuated, it pulls on the linkage 132, which in turn pulls on the pull member 134 and draws the crimp plate 128 proximally. The pull member 134 is rigid to ensure that there is enough force translated to the crimp plate 128 to crimp bands 150. Once the user releases trigger 112, the crimped band 150 would be attached to a hemorrhoid and the crimping mechanism would return to its original state, as seen in FIG. 9. The crimping mechanism may be spring loaded to return to its original state.

Figure 8:
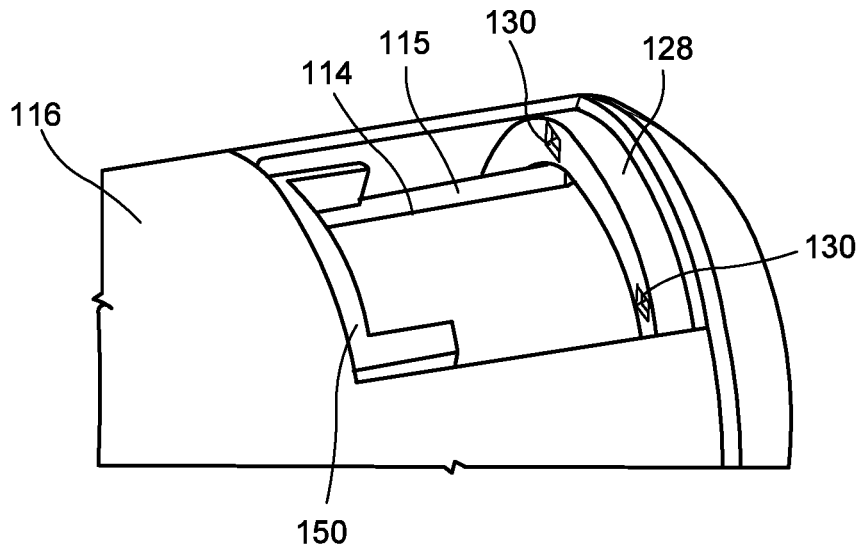
FIG. 8 shows a perspective view of a ligating window in the top of the device of FIG. 1 when the device is unactuated.

The middle portion 106 of the body 102 has a step 136 between the ligation band channel 124 and the window 118 such that a ligation band 150 that is pushed distally into the window 118 moves radially (inward toward a longitudinal axis of the device) into the window 118 a short distance and rests on a cut-away portion 115 of the inner cylinder 114, as shown in FIGS. 8-9. The device 100 is ready to deploy the band 150 when the band 150 is seated in the window 118 and the crimp plate 128 is in the distal position. Actuating the trigger 112 retracts the crimp plate 128 and deforms the band 150 against the step 136. Thus, it may be seen that the step 136 acts as an abutment surface against which the movable crimp plate 128, acting as an anvil, crimps the band 150.

Figure 10:
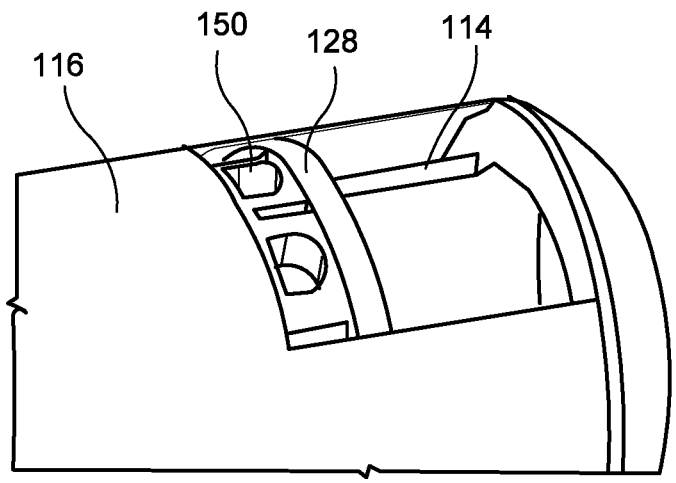
FIG. 10 shows a perspective view of the ligating window in the top of the device of FIG. 1 when the device is actuated.
Figure 11:
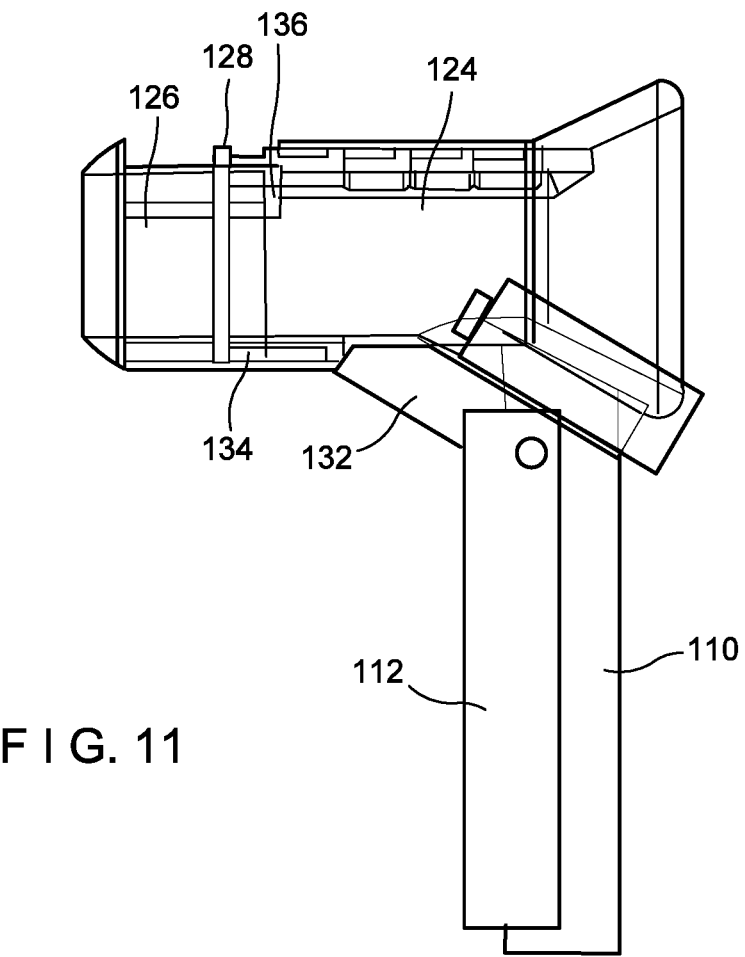
FIG. 11 shows a transparent side view of the device of FIG. 1 when the device is actuated.

The shape into which the band 150 of this embodiment is deformed is, in this particular embodiment, a function of the curvature of the lateral side of the band 150 and the interaction between the end of the longitudinal sides of the band 150 and the indents 130 in the crimp plate. In the embodiment shown in FIG. 10, the ends of the longitudinal sides of the band 150 are inserted into the indents 130 as the crimp plate 128 moves proximally. The indents 130 provide a temporary fixed lateral position for the ends of the longitudinal sides and the curvature of the band 150 causes the band 150 to initially bend outward. As the crimp plate 128 continues moving proximally the longitudinal sides of the band 150 are bent inward into the deformed shape of FIG. 10. The crimp plate 128 has a limiting stroke that would not close within the entire window. The limiting stroke allows for treatment of late stage hemorrhoids, so that banding by the stem of the hemorrhoid and crimping the band 150 into the deformed shape collapses those structures and prevents puncturing of the hemorrhoid. It is important to note however, that the resulting shape of band 150 may not deform completely when tissue is within a cavity of the band 150.

The aforementioned configuration of the band 150 and crimp plate 128 is one embodiment of the present disclosure. In other embodiments, the band 150 may be deformed into different shapes as a function of altering the parameters of the device 100. For example, the crimp plate 128 may not have indents 130, the longitudinal sides of the band 150 may be longer or shorter, the crimp plate 128 may be limited in the extent of its proximal movement, etc.

Once the band 150 is deformed, releasing the trigger 112 unseats the band 150 from the window 118. When the banded hemorrhoid is no longer in the window 118 a second ligation band 150 may be pushed into the window 118 to reload the device 100. The device 100 may then be situated to receive a second hemorrhoid in the window 118.

Figure 12:
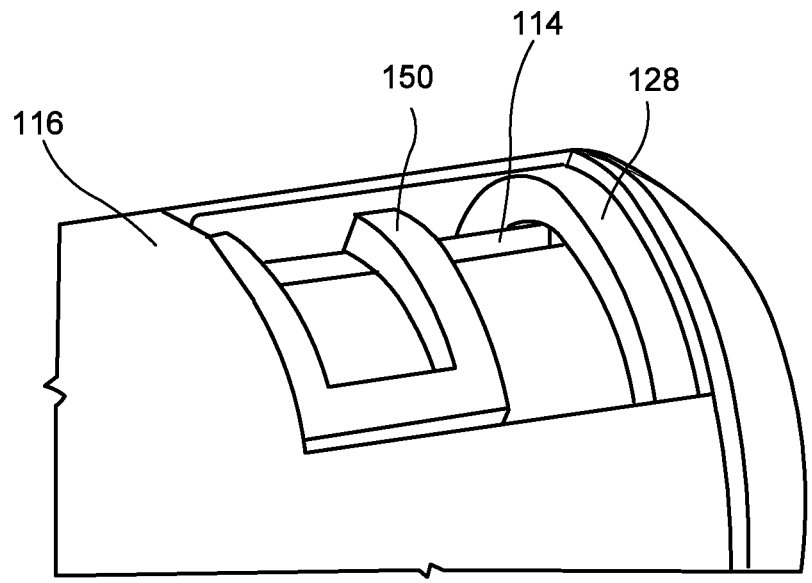
FIG. 12 shows an alternate embodiment of the ligation bands of the device of FIG. 1 when the device is unactuated.
Figure 13:
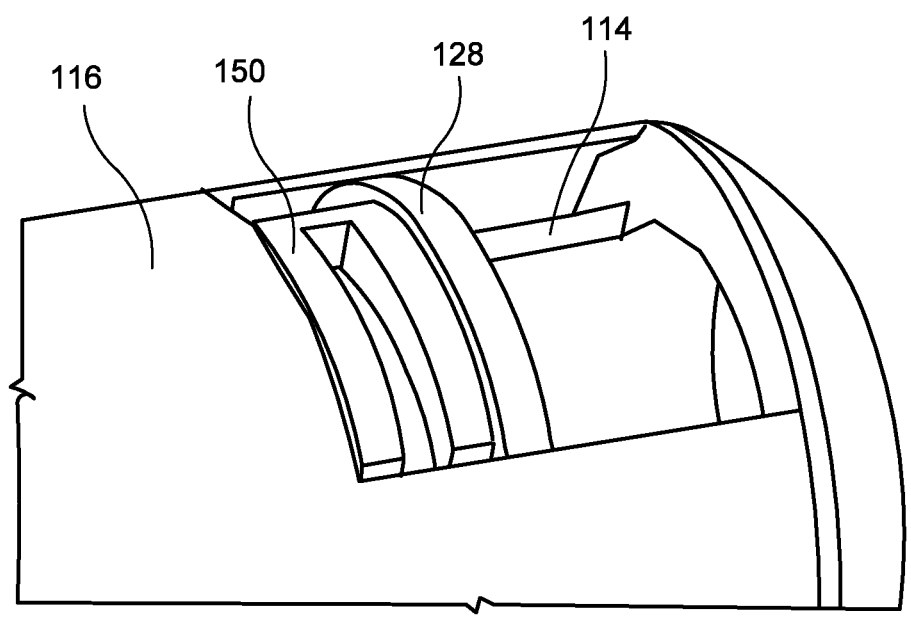
FIG. 13 shows the alternate embodiment of the ligation bands of the device of FIG. 1 when the device is actuated.

In a second embodiment, the ligation bands 150 are configured to be loaded in the ligation band channel 124 with the open side of the C-shape directed sideways, as shown in FIG. 12. In other words, the ligation bands 150 in the second embodiment are rotated 90° in either direction with respect to the ligation bands 150 in the first embodiment. The bands 150 in the second embodiment have two lateral sides extending off of a longitudinal side, similar to the first embodiment. However, unlike the first embodiment, the two lateral sides have the arced shape and the longitudinal side is substantially straight, such that the sideways C-shape may rest on the exterior of the inner cylinder 114 when the band 150 is loaded in the channel 124. The second embodiment of the ligation bands 150 may be used to create a different crimp shape, as shown in FIG. 13. The crimp shape of the second embodiment is a longitudinal flattening of the C-shape wherein the longitudinal side of the C-shape is bent inward. The C-shape bending is controlled by the same limiting stroke as the first embodiment.

Figure 14:
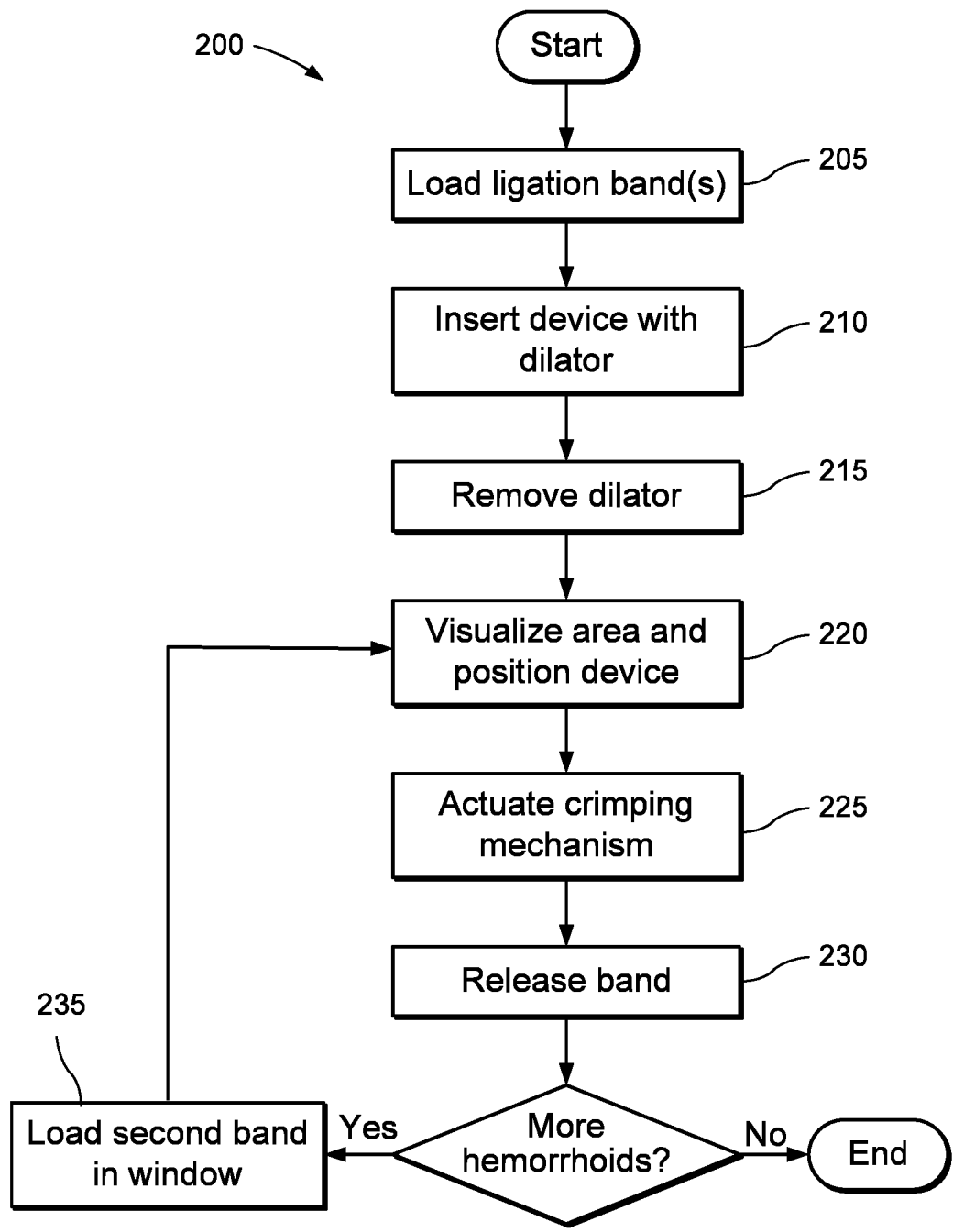
FIG. 14 shows a method for ligating hemorrhoids using the anoscope device of FIG. 1.

FIG. 14 shows a method 200 for ligating hemorrhoids of a patient using the anoscope device 100 of FIG. 1. In 205, at least one ligation band 150 is loaded in the ligation band channel 124 of the body 102. The band(s) 150 are preferably loaded prior to insertion of the device 100 into the anal cavity of the patient, however, the band(s) 150 may be loaded at any point prior to actuating the crimping mechanism.

In 210, the anoscope device 100, with the dilator 120 inserted into the interior of the body 102, is inserted into the anus of the patient to dilate the anal cavity. In 215, the dilator 120 is removed from the body 102, opening the window 118 and the distal end 104 to visualize the hemorrhoid treatment area.

In 220, the operating physician visualizes the treatment area and positions the device 100 to receive a hemorrhoid in the window 118. Once properly positioned, in 225, the trigger 112 is actuated to draw the crimp plate 128 proximally in the crimp plate channel 126 and deform the loaded band 150 around the base of the hemorrhoid.

In 230, the trigger 112 is released to release the crimp plate 128 to its distal position and unseat the band 150 from the window 118. If no more hemorrhoids remain to be treated the device may be removed. If further hemorrhoids remain to be treated, in 235, the window 118 may be loaded with a second ligation band 150 and steps 220-230 may be repeated. The device 100 is repositioned and a second hemorrhoid may be treated with the second band. The steps may repeat until there are no further hemorrhoids remaining to be treated.

It will be apparent to those skilled in the art that various modifications may be made in the present disclosure, without departing from the scope of the disclosure.

The invention claimed is:
1. A device, comprising:
an elongated hollow member with a window for receiving tissue in an interior of the hollow member;
a crimp plate channel extending from a proximal end of the window to a distal end of the window;
a rigid member slidably coupled to the hollow member; and
an actuation mechanism configured to move the rigid member longitudinally along a longitudinal axis through at least part of the window,
wherein the rigid member includes a ring-shaped crimp plate housed in the crimp plate channel and
wherein the rigid member is configured so that, when a ligation band is adjacent to the window and the rigid member is moved relative to the hollow member, the rigid member deforms the ligation band from an open position into a closed position around tissue received in the window.

2. The device of claim 1, further comprising:
a dilator configured to be inserted into the hollow member.

3. The device of claim 1, further comprising:
a light source directed towards the window.

4. The device of claim 1, wherein the ligation band is made of a metal.

5. The device of claim 1, wherein the ligation band is curved into a C-shape with an open side.

6. The device of claim 5, wherein the ligation band is loaded with the open side of the C-shape facing distally, the C-shape being formed of a lateral side with two longitudinal sides extending from either end of the lateral side.

7. The device of claim 5, wherein the ligation band is loaded with the open side of the C-shape directed transverse to the longitudinal axis, the C-shape being formed of a longitudinal side with two lateral sides extending from either end of the longitudinal side.

8. The device of claim 1, wherein the hollow member includes a tapered distal portion, a flared proximal base portion, and an elongated middle portion.

9. The device of claim 8, wherein the hollow member includes an inner cylinder and an outer cylinder separated from one another via an annular space.

10. The device of claim 9, further comprising:
a ligation band channel extending from a proximal end of the middle portion to a proximal end of the window, opening into the window.

11. The device of claim 10, wherein the ligation band channel is configured to house a plurality of ligation bands.

12. The device of claim 1, further comprising:
indents located in the crimp plate configured to deform the ligation band into a predetermined pattern.

13. The device of claim 1, further comprising:
a safety stop located on the actuation mechanism to prevent deformation of the ligation band during loading and prior to deployment.

14. A method comprising:
inserting into an anal cavity, a device including an elongated elbow hollow member, the hollow member including a window for receiving tissue in an interior of the hollow member; and
actuating an actuation mechanism of the device configured to move a rigid member longitudinally through at least a part of the window, the rigid member being slidably coupled to the hollow member,
wherein, the rigid member is configured so that, when a ligation band is adjacent to the window and rigid member is moved relative to the hollow member, the rigid member deforms the ligation band from an open position into a closed position around tissue received in the window,
wherein the device further includes a crimp plate channel extending from a proximal end of the window to a distal end of the window, and
wherein the rigid member includes a ring-shaped crimp plate housed in the crimp plate channel.

15. The method of claim 14, further comprising:
inserting a dilator into the device through the hollow member prior to insertion of the device into the anal cavity; and
removing the dilator after the device is inserted into a desired position.

16. The method of claim 14, further comprising:
illuminating a first target area via a light source to align the window of the hollow member with a first target portion of tissue.

17. The method of claim 14, further comprising:
releasing a safety stop on the actuation mechanism to move the rigid member longitudinally through at least part of the window.

18. The method of claim 14, further comprising:
visualizing a second target area;
rotating the hollow member independently of the actuation mechanism;
aligning the window with the second target area;
drawing a second target portion of tissue into the device through the window; and
actuating the actuation mechanism to deform the ligation band from the open position into the closed position around the second target portion of tissue.

* * * * *